Figure 1:
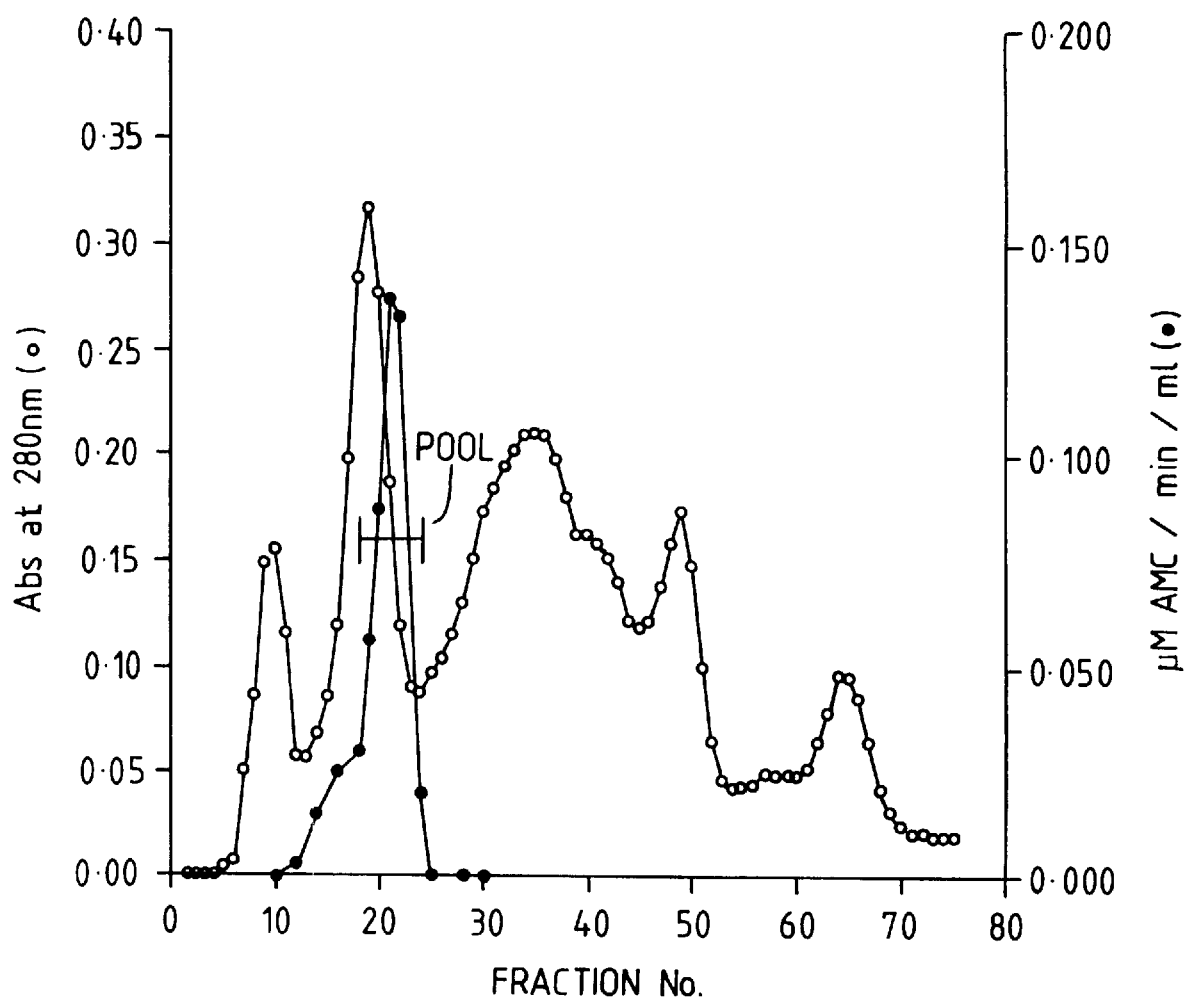

United States Patent [19]
Dalton et al.

[11] Patent Number: 5,885,814
[45] Date of Patent: Mar. 23, 1999

[54] VACCINE CONTAINING A SERINE PROTEASE

[75] Inventors: John P. Dalton, Dublin, Ireland; Stuart J. Andrews, Staines, England

[73] Assignee: Mallinckrodt Veterinary, Inc., Mundelein, Ill.

[21] Appl. No.: 564,091

[22] PCT Filed: Jun. 14, 1994

[86] PCT No.: PCT/GB94/01274

§ 371 Date: Apr. 26, 1996

§ 102(e) Date: Apr. 26, 1996

[87] PCT Pub. No.: WO94/28925

PCT Pub. Date: Dec. 22, 1994

[30] Foreign Application Priority Data

Jun. 15, 1993 [GB] United Kingdom ............... 9312324

[51] Int. Cl.⁶ .................. C12N 9/48; A61K 38/48
[52] U.S. Cl. .................. 435/183; 435/69.1; 435/69.3; 435/212; 424/265.1; 424/266.1; 424/94.1; 424/184.1; 424/94.64; 424/140.1; 424/151.1; 530/350; 530/403; 530/412; 530/413; 530/414; 530/416; 536/23.1; 536/23.2; 536/23.5; 536/23.7; 514/2; 514/21
[58] Field of Search .................. 424/265.1, 94.1, 424/184.1, 94.64, 140.1, 515.1, 266.1; 435/69.1, 69.3, 183, 212; 514/2, 21; 530/350, 403, 412, 414, 416, 413; 536/23.1, 23.2, 23.5, 23.7; 204/182.8

[56] References Cited

U.S. PATENT DOCUMENTS 4,879,213 11/1989 Fox et al. .

FOREIGN PATENT DOCUMENTS 9003433 4/1990 WIPO .

OTHER PUBLICATIONS

Plotein et al. (1988) Vaccines, WB Saunders Co., Philadelphia pp. 570–571.

Burgess et al (1990) J. Cell Biol. vol. 111, 2129–2138 Lehuizer Biochemistry, 2nd ed. Worth Publishers Inc. p. 63.

Lazen et al. (1988) Mol. and Cell Biol. vol. 8(3), 1247–1252.

Sea–Hui (1988) J. Biol–Chem. 263, 6613–18.

Bogitsh et al (1983) J. Parasital vol. 69, 106–10.

Waderl. et al (1986) IEBS Lett. vol 209, 330–334.

*Primary Examiner*—Paul K. Hutzell
*Assistant Examiner*—Khalid Masood
*Attorney, Agent, or Firm*—Rothwell, Figg, Ernst & Kurz

[57] ABSTRACT

Disclosed is the invention relates to the use of serine protease having peptidyl peptidase activity in the formulation of vaccines for combating helminth parasites. The protease is derived from a fluke *Fasciola hepatica*.

1 Claim, 4 Drawing Sheets

PURIFICATION OF DIPEPTIDYL PEPTIDASE (A) SEPHACRYL S200

PURIFICATION OF DIPEPTIDYL PEPTIDASE (B) DEAE SEPHAROSE

VACCINE CONTAINING A SERINE PROTEASE

This application is a 371 of PCT/GB94/01274 filed Jun. 14, 1994 which claims priority under 35 U.S.C., 119 of Great Britain application 9312324.8 filed Jun. 15, 1993.

The invention relates to the use of a class of serine proteases as protective antigens against helminth parasites.

Each species of domestic animal can be parasitised by a number of different species of helminths, a process which usually causes disease. For example, the parasitic trematode *Fasciola hepatica* is known to be the cause of the economically important disease fascioliasis in ruminants, such as cattle and sheep. The parasite enters the mammalian host by penetrating the gut wall and spends approximately seven weeks feeding on and burrowing through the liver mass before migrating into the bile duct. Following infection, development of immunity in the host can be poor and resistance to reinfection in already infected hosts may be only partial or non-existent. Other parasitic flukes include *Fasciola gigantica* and Dicrocoelium spp. and also Paramphistomum spp.

Problems are also caused by nematodes such as hookworms (e.g. Necator, Ancylostoma, Uncinaria and Bunostomum spp.).

Of the blood feeding nematodes the genus Haemonchus causes anaemia and weight loss and if untreated frequently leads to death. Animals infected with the related non-blood feeding nematode Ostertagia similarly fail to thrive and may die if untreated.

Other parasitic worms of economic importance include the various species of the following helminth genera: Trichostrongylus, Nematodirus, Dictyocaulus, Cooperia, Ascaris, Dirofilaria, Trichuris and Strongylus. In addition to domestic livestock, pets and humans may also be infected, not infrequently with fatal results and helminth infections and infestations thus pose a problem of considerable worldwide significance.

Control of helminth parasites of grazing livestock currently relies primarily on the use of anthelmintic drugs combined with pasture management. Such techniques are often unsatisfactory, firstly because anthelmintic drugs may have to be administered frequently, secondly because resistance against anthelmintic drugs is—becoming increasingly widespread and thirdly because appropriate pasture management is often not possible on some farms and even where it is, it can place constraints on the best use of available grazing.

Numerous attempts have been made to control helminth parasites of domestic animals by immunological means. With very few exceptions (e.g. the cattle lungworm, *Dictyocaulus viviparus*) this has not proved possible.

A vaccine against *F.hepatica* has been proposed in WO90/08819 comprising a glutathione-S-transferase from *F.hepatica* as antigenic material.

Bennett (UK Patent No. 2169606B) extracted various antigens from Fasciola organisms by a process which separates antigens specific to the juvenile stage from antigens present throughout the juvenile and adult stages.

Furthermore crude in vitro excretory/secretory (E/S) products can under some circumstances confer immunity on rats (Rajasekariah et al, Parasitol. 79 (1979), p. 393–400).

It has now been found that *F.hepatica* excretory/secretory products contain a novel protein having a dipeptidyl peptidase (DPP) type of activity described in more detail hereinafter. This discovery opens up the possibility of vaccines against *F.hepatica* and other helminths based on the use of the novel enzyme as an antigen and/or corresponding enzymes produced by other helminth parasites.

Accordingly a first aspect of the present invention provides a vaccine for use in combating a parasitic infestation of helminths in a mammal wherein the antigenic material comprises a serine protease having dipeptidyl peptidase-like activity, in at least partially purified form, or an antigenic fragment or epitope thereof, together with a carrier and/or adjuvant.

The invention also provides a method of combating a parasitic infestation of helminths in a mammal comprising administering to said mammal a vaccine according to the invention as hereinbefore defined in an amount effective to combat said infestation.

The mammal is preferably a ruminant, for example cattle or sheep, but the vaccine and method of the invention may also find application in humans.

Preferably the dipeptidyl peptidase-like protease is derived from flukes such as Fasciola or Dicrocoelium, in particular from the liver fluke *Fasciola hepatica*. Alternatively it is preferred that the dipeptidyl peptidase should be capable of stimulating an immune response which will be effective against Fasciola or Dicrocoelium, in particular *F. hepatica* and *F. gigantica*, such dipeptidyl peptidase-like proteases from other species as are capable of conferring a cross-protective immune response thus forming a particularly preferred aspect of the invention.

The *F.hepatica* dipeptidyl peptidase-like protease shown hereinafter to possess a molecular weight of approximately 200 KDa by sodium dodecyl sulphate polyacrylamide gel electrophoresis under reducing and non-reducing conditions and by gel filtration chromatography is particularly preferred for use in the vaccine and method of the invention and as a novel protein itself forms a further aspect of the invention.

The dipeptidyl peptidase incorporated in the vaccine according to the invention is in at least partially purified form. Preferably the dipeptidyl peptidase comprises at least 75% of the total excretory/secretory proteins present in the vaccine and more preferably the dipeptidyl peptidase is at least 95% pure. It will be appreciated that once dipeptidyl peptidase of at least 95% purity has been obtained it can be admixed with one or more further purified antigenic proteins, including one or more further excretory/secretory proteins, to form a polyvalent vaccine.

A preferred form of polyvalent vaccine according to the invention will contain a dipeptidyl peptidase as referred to above in combination with a Cathepsin L-type antigen as described in more detail in International Patent Application No. WO94/09142. Such a polyvalent vaccine will, by inducing immunity in the host species against two separate aspects of the invading helminth parasite, significantly increase the likelihood of protection against the helminth and significantly reduce the chances of infestation occurring.

Dipeptidyl peptidases have been isolated from a mammalian source (J. Biol. Chem. 263 (1988), pages 6613–6618) and were characterised by an ability to cleave dipeptide substrates. Four different specificities were noted and are referred to in more detail hereinafter. The dipeptidyl peptidases of the present invention are likewise characterised by their ability to cleave fluorogen linked dipeptide substrates while showing no activity against fluorogen linked mono amino acid substrates thus demonstrating that the enzymes cleave amino acids in pairs from the N-terminus of the substrate.

The vaccines according to the invention may be formulated with conventional carriers and/or adjuvants and the invention also provides a process for the preparation of the vaccines comprising bringing into association purified dipeptidyl peptidase or an antigenic fragment or epitope thereof and one or more adjuvants or carriers. Suitable adjuvants include aluminium hydroxide, saponin (ISCOMs), quil A and more purified forms thereof, muramyl dipeptide, mineral and vegetable oils, DEAE dextran, nonionic block copolymers or liposomes such as Novasomes (Trade Mark of Micro Vesicular Systems Inc.), in the presence of one or more pharmaceutically acceptable carriers or diluents. Carriers for peptide sequences corresponding to epitopes of dipeptidyl peptidases according to the invention can be proteins such as Hepatitis B core antigen multiple antigen peptide or lipopeptides such as tripalmitoyl-S-glycerylcysteinylserylserine ($P_3CSS$). Suitable diluents include liquid media such as saline solution appropriate for use as vehicles. Additional components such as preservatives may be included.

Administration of the vaccine to the host species may be achieved by any of the conventional routes, e.g. orally or parenterally such as by intramuscular injection, optionally at intervals e.g. two injections at a 7–35 day interval. A suitable dose when administered by injection might be such as to give an amount of dipeptidyl peptidase protein within the range 10–500 μg.

While the dipeptidyl peptidase for use in the vaccine according to the invention may be prepared by isolation from the excretory/secretory products of adult and/or juvenile helminths, it may also be convenient to prepare it by recombinant DNA techniques with the known advantages which such techniques give in terms of scaling-up of production and reproducibility. Thus the invention also provides a dipeptidyl peptidase or a proenzyme therefor or an antigenic fragment or epitope thereof, produced by means of recombinant DNA techniques.

Additional aspects of the invention related to the above include DNA molecules encoding for dipeptidyl peptidases or antigenic fragments or epitopes thereof; vectors containing one or more such DNA sequences; host cells, for example bacteria such as *E. coli* or more preferably eukaryotic cells, transformed by such vectors, for example by a baculovirus vector; and processes for preparing recombinant dipeptidyl peptidase or antigenic fragments or epitopes thereof comprising culturing such transformed host cells and isolating said dipeptidyl peptidase or fragment or epitope from the cultured cells.

An alternative live or inactivated vaccine formulation may comprise an attenuated or virulent virus or a host cell, e.g. a microorganism such as a bacterium, having inserted therein a nucleic acid molecule (e.g. a DNA molecule) according to the invention for stimulation of an immune response directed against polypeptides encoded by the inserted nucleic acid molecule. A bacterial vector which elicits local gut mucosal immunity to a fluke antigen which then blocks juvenile fluke migration is particularly preferred, notably invasive species such as Salmonella species.

Additional antigenic materials may also be present in the vaccine thus giving an enhanced protective effect against the helminth parasite in question or a combined protective effect against one or more additional parasitic infestations.

A yet further aspect of the invention provides a monoclonal or polyclonal antibody capable of inducing immunity to a dipeptidyl peptidase in a mammal when administered to said mammal, the antibody having an affinity for the variable region of one or more further antibodies, said further antibodies having an affinity for said dipeptidyl peptidase.

This approach, the so-called "anti-idiotype" approach, permits formulation of a vaccine which will dispense entirely with the original antigen and may offer even greater advantages in terms of safety, avoidance of side effects and convenience of manufacture.

The invention is illustrated by the following examples:

1) Preparation of in vitro released products

Mature *Fasciola hepatica* flukes were removed from the bile ducts of bovine livers obtained at an abattoir in Ireland. The flukes were washed six times in phosphate buffered saline (PBS), pH 7.3, and then maintained in Roswell Park Memorial Institute (RPMI)—1640, pH 7.3, containing 2% glucose, 30 mM Hepes and 25 mg/l gentamycin overnight at 37° C. The medium (excretory/secretory or E/S products) was then removed, frozen and stored at −20° C.

2) Purification of dipeptidylpeptidase-like protease

Five hundred ml of adult fluke E/S products were concentrated to 10 ml in an Amicon 8400 Ultrafiltration unit using a UM 3 membrane. The sample was removed and centrifuged at 15000×g for 45 mins. The supernatant was then applied to a 300 ml Sephacryl S200 column equilibrated in 0.1M tris, pH 7.0. The column was eluted with 0.1M tris, pH 7,0. Fractions (5 ml) were collected after the void volume of 100 ml had been passed. The eluate was monitored for protein content at 280 nm and the fractions were assayed for dipeptidyl peptidase activity using the substrate Gly-Pro-AMC in 0.25M HEPES, pH 6.8 (FIG. 1) (AMC is 7-amino-4-methylcoumarin). Fractions containing DPP activity were pooled (approx. 40 ml) and concentrated to 8 ml in an Amicon ultrafiltration unit using a UM3 membrane. The concentrate was divided into eight 1 ml fractions and stored frozen at −20° C.

Figure 2:
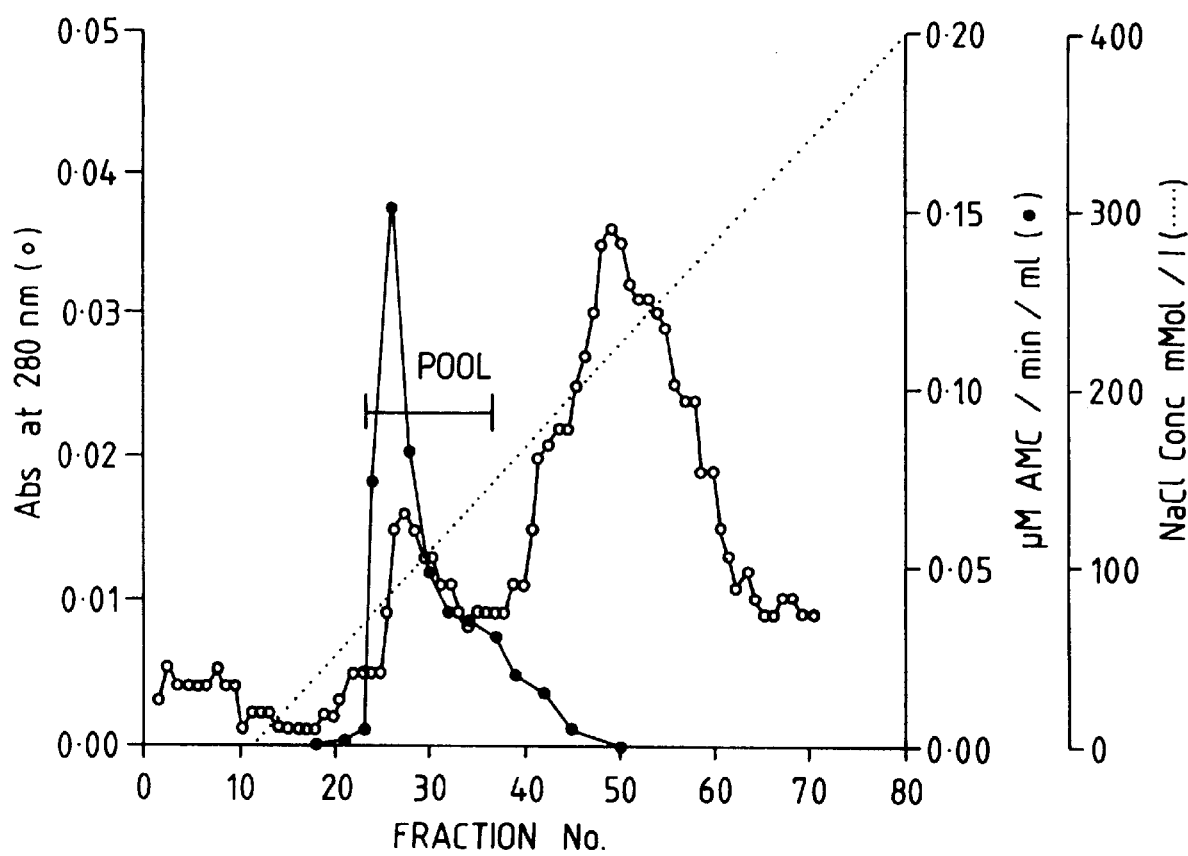

One ml of concentrate was thawed and dialysed against 0.025M HEPES, pH 6.8, and applied to a 12 ml diethyl amino ethyl Sepharose column (1.5×8 cm) equilibrated in the same buffer. The column was eluted with a salt gradient (0–400 mm NaCl in equilibration buffer) and fractions (2.5 ml) were collected. The eluate was monitored at OD 280 nm and two peaks were obtained. Fractions were assayed for DPP activity using the Gly-Pro-AMC substrate. The DPP activity was present in the first peak and eluted at approximately 100 mM NaCl (FIG. 2). These fractions were pooled, concentrated in an Amicon Ultrafiltration unit, dialysed against deionised water, freeze-dried and stored at −20° C.

3) Molecular size estimation of dipeptidyl peptidase

Figure 3:
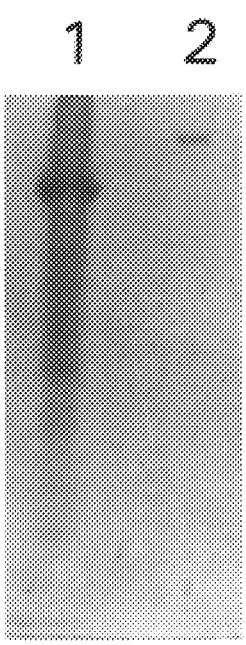

Gel filtration chromatography carried out on Sephacryl S200 as described above (using immunoglobulin, 150 kDa, albumin, 68 kDa, ovalbumin, 45 kDa and β-lactoglobulin, 18.4 kDa, as standards) indicated a molecular size of approximately 200 kDa for the peak of DPP-like activity. Samples of purified protease were also analysed by 0.1% SDS 10% polyacrylamide gel electrophoresis under non-reducing conditions. The molecular size was estimated as 200 kDa (see FIG. 3, lane 1 E/S products, lane 2 purified protease). Analysis by reducing 0.1% SDS-10% polyacrylamide gel electrophoresis revealed a similar molecular size indicating that the protease consists of a single polypeptide chain.

4) Characterisation of pH optimum for dipeptidyl peptidase-like activity

The activity of the protease on both gly-pro-AMC and lys-ala-AMC substrates was estimated over the pH range 4.5 to 8.2. The pH for optimum activity was determined to be pH 6.8. It was also demonstrated that the activity of the protease was optimum in HEPES buffer; both tris and phosphate buffers adversely affected the activity (see Table 1). HEPES buffer (50 mM pH 6.8) has therefore been the routine buffer used in all experiments and purification procedures.

TABLE 1

DPP-like activity using different buffer and pH systems

| Buffer (pH) | Lys—Ala—AMC % activity | Gly—Pro—AMC % activity |
|---|---|---|
| Hepes 50 mM (6.8) | 100 | 100 |
| Hepes 50 mM (7.6) | 61 | 20 |
| Hepes 50 mM (8.2) | 22 | 1 |
| Sodium citrate 0.1M (4.5) | 11 | 8 |
| Tris HCl 0.1M (6.8) | 10 | 15 |
| PBS 0.1M (7.2) | 14 | 35 |

5) Substrate specificity of protease

Peptide bond specificity was investigated using several fluorogenic peptide substrates that have previously been used to categorise mammalian dipeptidyl peptidases I, II, III and IV (J. Biol Chem. 263 (1989), pages 6613–6618). These substrates included gly-arg-AMC (DPP-I), lys-ala-AMC (DPP-II), arg-arg-AMC (DPP-III) and gly-pro-AMC (DPP-IV).

The assay mixture contained 200 μl of 20 μM substrate, 100 μl of enzyme solution and 900 μl of 50 mM Hepes, pH 6.8. The reaction was allowed to proceed at 37° C. and stopped by the addition of 200 μl of 1.7M acetic acid. The liberated AMC was measured in a fluorometer with excitation and emission wavelengths of 370 nm and 440 nm, respectively.

The liver fluke protease selectively cleaved lys-ala-AMC and gly-pro-AMC, the Michealis-Menton constants ($K_m$) for these substrates being 58 and 25 μM, respectively. The protease did not cleave the substrates gly-arg-AMC and arg-arg-AMC. These data demonstrate that the protease is novel; a DPP-like enzyme which has such similar affinities ($K_m$) for these two substrates has not previously been described. The fluke enzyme shows both DPP-II and DPP-IV type activity if the classification applied to mammalian DPPs is used. The enzyme showed no activity against various aminopeptidase substrates including lys-, ala-, leu- and pro-AMC. These data demonstrate the specificity of the enzyme for dipeptide substrates.

6) Direct visualisation of DPP-like activity in polyacrylamide gels

Figure 4:
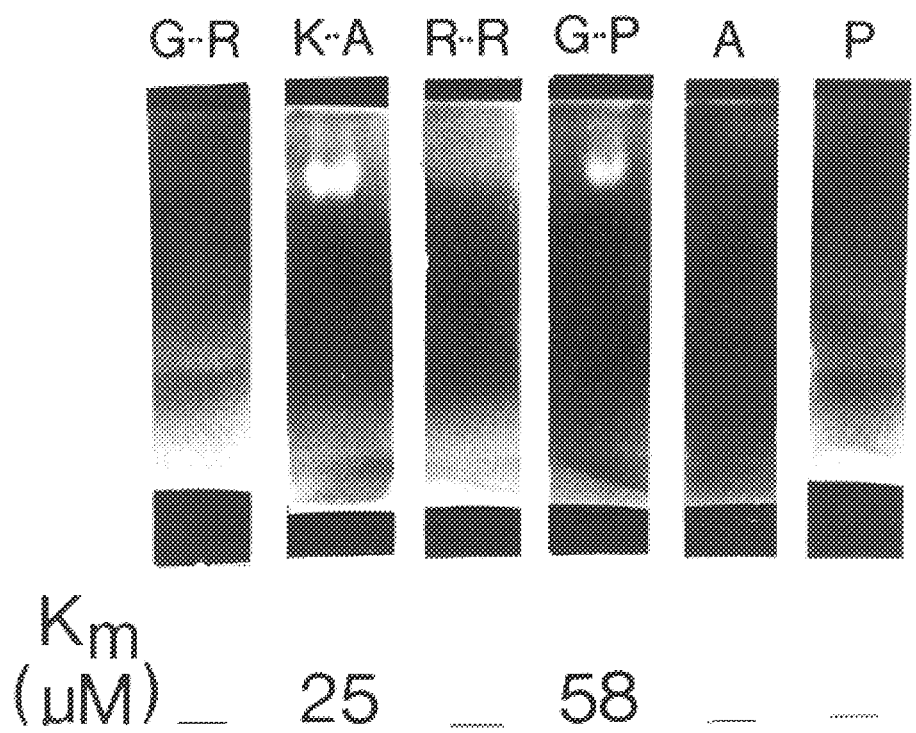

To verify that a single protease with both DPP2- and DPP4-like activity, was present in liver fluke E/S products, samples of E/S were electrophoretically separated in 10% native polyacrylamide gels (prepared as described above with the exception that no SDS was added to samples or gels) and following electrophoresis the gels were immersed in solutions of the various fluorogen linked substrates (50 μM in 50 mM HEPES). After incubation the gels were then placed on a UV transilluminator and photographed using polaroid film. Only a single band was visualised, with an identical mobility, using the substrates gly-pro-AMC and lys-ala-AMC. No bands were visualised using gly-arg-AMC, arg-arg-AMC, ala-AMC and pro-AMC (FIG. 4 and table 2 below). Purified DPP-like protease was also shown to migrate similarly in these gels and exhibited a similar substrate specificity G-R, K-A, R-R, G-P, A and P are respectively Gly-Arg-AMC, Lys-Ala-AMC, Arg-Arg-AMC, Gly-Pro-AMC, Ala-AMC and Pro-AMC. The $K_m$ values are as given in the previous section.

TABLE 2

Substrate specificity of DPP-like protease from
F. hepatica E/S products

| Substrate | Activity (Arbitrary units) |
|---|---|
| Gly—Arg—AMC (DPP I) | – |
| Lys—Ala—AMC (DPP II) | ++++ |
| Arg—Arg—AMC (DPP III) | – |
| Gly—Pro—AMC (DPP IV) | +++ |
| Pro—AMC | – |
| Ala—AMC | – |

7) Inhibitor studies

The effect of various metal ions on the hydrolytic activity of the enzyme was examined using both gly-pro-AMC and lys-ala-AMC as substrates in assays as described above. The results demonstrate that metal ions such as calcium, magnesium and manganese have little effect on enzyme activity whereas zinc at 1 mM concentration inhibits activity by >85%. The heavy metals iron, mercury, cadmium and cobalt all inhibit enzyme activity to >90% at a concentration of 5 mM whereas lead showed <20% inhibition at this concentration. The enzyme was not inhibited by the proteinase inhibitors EDTA, pepstatin and aprotinin indicating that the enzyme is not a metallo- or aspartyl protease. The enzyme is inhibited by phenylmethyl sulfonyl fluoride (PMSF), an inhibitor of serine and cysteinyl proteinases; however, since no activation of the enzyme is observed with thiol activating agents such as cysteine, dithiothreitol and mercaptoethanol the enzyme does not appear to be a cysteinyl proteinase. Benzamidine, an inhibitor of serine proteinases, inhibits the activity of the DPP. The conclusion is that the liver fluke enzyme is a serine proteinase. These inhibition studies also support our conclusion that a single enzyme cleaves both gly-pro-AMC and lys-ala-AMC substrates as a similar inhibitor profile was observed when either substrate is used (Table 3).

TABLE 3

Effects of heavy metals and inhibitors on DPP activity

| Substance | Concentration (mM) | Activity remaining (%) Lys—Ala | Activity remaining (%) Gly—Pro |
|---|---|---|---|
| None |  | 100 | 100 |
| Mn | 1 | 66 | 66 |
| Mn | 0.5 | 104 | 102 |
| Mg | 1 | 76 | 78 |
| Mg | 0.5 | 105 | 116 |
| Ca | 1 | 62 | 57 |
| Ca | 0.5 | 96 | 133 |
| Zn | 1 | 14 | 3 |
| Zn | 0.5 | 37 | 80 |
| Pb | 1 | 103 | 109 |
| Pb | 5 | 82 | 70 |
| Cd | 1 | 19 | 26 |
| Cd | 5 | 5 | 6 |
| Co | 1 | 28 | 20 |
| Co | 5 | 6 | 4 |
| Fe | 1 | 5 | 6 |
| Fe | 5 | 2 | 2 |
| Hg | 1 | 4 | 7 |
| Hg | 5 | 2 | 5 |
| 2-Mercaptoethanol | 1 | 75 | 87 |
| EDTA | 2 | 121 | 108 |
| Pepstatin | 5 μg/ml | 92 | 108 |
| Aprotin | 5 μg/ml | 116 | 109 |
| PMSF | 2 | 3 | 2 |

TABLE 3-continued

Effects of heavy metals and inhibitors on DPP activity

| Substance | Concentration (mM) | Activity remaining (%) Lys—Ala | Gly—Pro |
|---|---|---|---|
| DTT | 1 | 62 | 90 |
| DTT | 0.5 | 61 | 77 |
| Cysteine | 1 | 105 | 104 |
| Cysteine | 0.5 | 112 | 104 |
| Benzamidine | 1 | ND | 77 |
| Benzamidine | 5 | ND | 35 |
| Benzamidine | 10 | ND | 23 |
| Puromycin | 0.1 | 100 | 100 |
| Puromycin | 0.02 | 100 | 100 |
| Bacitracin | 0.1 | 100 | 100 |
| Bacitracin | 0.02 | 100 | 100 |

8) Inhibition studies with puromycin and bacitracin

Mammalian DPP2 and DPP4 can be distinguished using the inhibitors puromycin and bacitracin; puromycin will inhibit DPP2 only whilst bacitracin inhibits DPP4 only (J. Biol. Chem. 263 (1988), 6613–6618). When both these substrates were tested in inhibition studies with the fluke enzyme neither showed any inhibitory effect highlighting another difference between mammalian DPPs and the fluke enzyme (see Table 3 above).

We claim:

1. An Isolated dipeptidyl peptidase of *Fasciola hepatica* origin having molecular weight of 200 kDa by sodium dodecyl sulphate polyacrylamide gel electrophoresis under reducing and non-reducing conditions which is capable of selectively cleaving gly-pro and lys-ala dipeptide substrates.

* * * * *